(12) United States Patent
Jasra et al.

(10) Patent No.: US 7,345,182 B2
(45) Date of Patent: Mar. 18, 2008

(54) CATALYTIC EPOXIDATION OF STYRENE WITH MOLECULAR OXYGEN USING METAL ION EXCHANGED ZEOLITES

(75) Inventors: Raksh Vir Jasra, Bhavnagar (IN); Jince Sebastian, Bhavnagar (IN)

(73) Assignee: Central Salt and Marine Chemicals Research Institute, Bhavnagar (IN)

( * ) Notice: Subject to any disclaimer, the term of this patent is extended or adjusted under 35 U.S.C. 154(b) by 0 days.

(21) Appl. No.: 11/375,697

(22) Filed: Mar. 14, 2006

(65) Prior Publication Data

US 2007/0149791 A1   Jun. 28, 2007

(30) Foreign Application Priority Data

Dec. 27, 2005   (IN) .................. 3486/DEL/2005

(51) Int. Cl.
*C07D 301/03* (2006.01)
(52) U.S. Cl. ..................................... 549/523
(58) Field of Classification Search .............. None
See application file for complete search history.

(56) References Cited

U.S. PATENT DOCUMENTS

| | | | |
|---|---|---|---|
| 3,806,467 A | 4/1974 | Koke et al. ............... 502/154 |
| 3,953,362 A | 4/1976 | Lines et al. ............... 502/160 |
| 4,157,346 A | 6/1979 | Lines et al. ............... 549/531 |
| 4,418,203 A | 11/1983 | Kim ........................... 549/531 |
| 4,864,041 A | 9/1989 | Hill ............................ 549/513 |
| 4,894,467 A | 1/1990 | Blum ......................... 549/534 |
| 5,041,569 A | 8/1991 | Enomoto et al. .......... 549/531 |
| 5,145,968 A | 9/1992 | Monnier et al. ......... 549/281.7 |
| 5,155,241 A | 10/1992 | Nishibe et al. ............ 549/531 |
| 5,939,568 A | 8/1999 | Sharpless et al. .......... 549/623 |
| 6,194,591 B1 | 2/2001 | Grey et al. ................. 549/533 |
| 6,534,661 B1 | 3/2003 | Zhou et al. ................ 549/531 |
| 2005/0065355 A1 | 3/2005 | Choudhary et al. ...... 549/529 |
| 2005/0113586 A1 | 5/2005 | Choudhary et al. ...... 549/529 |

OTHER PUBLICATIONS

Tang et al. Epoxidation of Styrene with molecular oxygen catalyzed by cobalt (II)-containing molecular sieves.□□Journal of Catalysis, 2005, vol. 230, p. 384-397.*
Liang et al. Iron-based heterogeneous catalysts for epoxidation of alkenes using molecular oxygen.□□Catalyst Communications, 2004,vol. 5, p. 665-669.*

* cited by examiner

*Primary Examiner*—Sikarl A. Witherspoon
(74) *Attorney, Agent, or Firm*—Westman, Champlin & Kelly, P.A.

(57) ABSTRACT

This invention provides a catalytic epoxidation of styrene to styrene oxide with molecular oxygen using cobalt containing zeolite. Catalytic epoxidation of styrene-to-styrene epoxide was carried out using molecular oxygen in presence of $Co^{2+}$ exchanged zeolites. Molecular oxygen from air is also useful for the epoxidation reaction at atmospheric pressure. The presence of adsorbed water molecules in the catalyst also increases the styrene conversion without affecting the styrene oxide selectivity. Various alkali and alkaline earth cationic promoters were introduced into the zeolite catalyst to increase the styrene oxide selectivity. The present invention explore the effect of adsorbed water molecules and alkali and alkaline earth metal cationic promoters in the cobalt exchanged zeolite catalyst, on the styrene conversion and styrene oxide selectivity for the catalytic epoxidation of styrene to styrene oxide with molecular oxygen.

8 Claims, No Drawings

CATALYTIC EPOXIDATION OF STYRENE WITH MOLECULAR OXYGEN USING METAL ION EXCHANGED ZEOLITES

FIELD OF THE INVENTION

The present invention relates to the catalytic epoxidation of styrene with molecular oxygen using metal ion exchanged zeolites.

More specifically, the invention relates to a catalyst and the catalytic process for epoxidation of styrene to styrene oxide using molecular oxygen/air in presence of cobalt exchanged zeolite catalyst having adsorbed water molecules and alkali and/or alkaline earth metal cationic promoters.

BACKGROUND OF THE INVENTION

Styrene oxide is used over a wide range of field, for example as a stabilizer for polymers, an ultraviolet ray absorber, a starting material in the preparation of drugs, a stabilizer for solvents, or as a starting material for phenethyl alcohol and phenethyl aldehyde which are useful as synthetic perfumes and sweetening materials.

For preparing styrene oxide by the epoxidation of styrene there generally is adopted a process in which styrene is epoxidised using an organic peracid. However, this process involves the following drawbacks and is not always satisfactory.

(1) During the reaction of oxidizing styrene with an organic peracid, the organic peracid is decomposed and there occurs an addition reaction of the resulting radical to styrene, thus resulting in that the selectivity of styrene oxide with respect to styrene is deteriorated.

(2) The resulting styrene oxide cleaves in the presence of an organic acid byproduced after the reaction, thereby producing an ester and a hydroxy compound, whereby the selectivity of styrene oxide with respect to styrene is deteriorated.

(3) Peracetic acid which is most easily available industrially among organic peracids is prepared by a so-called Daicel-Wacker process comprising air oxidation of acetaldehyde, but it is a very expensive oxidizing agent.

(4) In order to avoid a possible danger in the use of an organic peracid it is necessary to pay close attention to both operation and equipment.

In order to overcome these limitations, the conventional route for epoxidation of alkenes is being attempted to be replaced by environmental friendly re-usable heterogeneous catalysts and hydrogen peroxide/molecular oxygen as oxidant.

Y. W. Kobe in U.S. Pat. No. 3,806,467 (1974) proposed a process wherein an olefin and hydrogen peroxide are reacted in the presence of a bis(tri-n-methyltinoxy) molybdic acid catalyst to prepare an epoxide. However, as long as the working Examples thereof are reviewed, the yield of styrene oxide is a little lower than 3% (based on hydrogen peroxide) and thus this proposed process cannot be considered preferable as a styrene oxide preparing process. E. L. Lines et al. in U.S. Pat. No. 3,953,362 (1976) describes oxygen-containing molybdenum compound as catalysts for the epoxidation reaction of unsaturated organic compounds with peroxidic compounds such as hydrogen peroxide. In order to retard the co-production of undesirable organic compounds such as glycols, it is required to have no more than a minor amount of water present during oxidation. The main drawback of this invention is that the hydrogen peroxide using in the reaction must have less than 1 percent water in it.

E. L. Lines et al. in U.S. Pat. No. 4,157,346 (1979) describes an epoxidation method wherein an alkylene compound is reacted with a peroxidic compound, e.g., $H_2O_2$, in the presence of an improved molybdenum catalyst at 10 to 20 atmospheres pressure. The water which may be formed enhances the production of undesirable glycols, it desirable to maintain the amount of water to get epoxide selectivity. The main drawbacks of this invention are the high pressure required for the reaction and the contentious removal of the by-product water formed from the reaction mixture.

L. Kim in U.S. Pat. No. 4,418,203 (1983) describes a process for the epoxidation of olefins with hydrogen peroxide in a fluorinated alcoholic solvent using a catalyst selected from a group consisting of molybdenum, tungsten and rhenium and an organo metallic co-catalyst selected from the group consisting of organo tin, organo arsenic, organo antimony and organo germanium. The main drawback of this invention is the use of fluorinated alcoholic solvent for the reaction.

C. L. Hill in U.S. Pat. No. 4,864,041 (1989) A novel process for the homogenous oxidation of organic substrates is disclosed. This process uses a transition metal-substituted polyoxometalate catalyst, which in the presence of an oxygen donor, catalyses epoxidation reaction of the organic substrate. Typical oxygen donors used in this invention include $C_{1-30}$ alkyl hydroperoxides, hydrogen peroxide, $C_{6-30}$ iodosylarenes, $C_{1-30}$ amine N-oxides, $C_{1-30}$ peracids, hypochlorites, and other halogen oxyanions, oxaziridines, and highly oxidizing transition metal oxo compounds such as chromate, dichromate, permanganate, ruthenium and osmium tetroxides. The main drawback of this invention is the oxygen donor is required to use in equivalent to the amount of substrate or on a molar basis for the oxidation of the substrate.

P. R. Blum in U.S. Pat. No. 4,894,467 (1990) disclosed a process for making styrene oxide which comprises contacting styrene in the vapour phase with a molecular oxygen-containing gas over a silver metal catalyst containing a promoting amount of at least one alkali metal hydroxide selected from sodium, potassium and lithium hydroxides, on an inert solid inorganic support at contact times of from 0.6 to 10 seconds and temperatures from 200 to 350° C. The main drawback of this invention is that the reaction was carried out at vapour phase at high temperatures ranging from 200 to 350° C.

S. Enomoto et al. in U.S. Pat. No. 5,041,569 (1991) discloses a process for the styrene oxide preparation by reacting styrene and hydrogen peroxide in a heterogeneous system in the presence of a bis(tri-n-alkyltinoxy)molybdic acid and an amine such as ammonia, primary, secondary and tertiary methylamines, primary, secondary and tertiary ethylamines, primary, secondary and tertiary n-propylamines, primary, secondary and tertiary isopropylamines, primary, secondary and tertiary butylamines, primary, secondary and tertiary ethanolamines. The main drawback of this invention is that the process involves the use of amine promoters.

J. R. Monnier et al. in U.S. Pat. No. 5,145,968 (1992) disclosed a process for the selective monoepoxidation of styrene, styrene analogs, and styrene derivatives. Such compounds are contacted with an oxygen-containing gas in the presence of a promoted, supported silver catalyst at a pressure in the range of 0.1 up to 100 atmospheres, temperature in the range of 100 to 325° C. 0.5 to 75% conversion was obtained during the reaction. The main drawback of this invention is that the maximum conversion was only 75%.

K. Nishibe et al. in U.S. Pat. No. 5,155,241 (1992) describes a process for preparing Styrene oxide by reacting styrene and hydrogen peroxide in a heterogeneous system in the presence of a bis(tri-n-alkyltinoxy) molybdic acid catalyst and an inorganic anion as a promotor in the reaction. 62-77% conversion was observed and 45-100% selectivity was obtained. The main drawback of this invention is that the maximum conversion was only 77%.

K. B. Sharpless et al. in U.S. Pat. No. 5,939,568 (1999) discloses a rhenium-catalyzed epoxidation of olefinic substrates, accelerated by the accelerants having a nitrogenous aromatic heterocyclic structure. Use of the accelerants also enables the use of aqueous hydrogen peroxide as an oxidant. To achieve optimum acceleration, the accelerant should have a concentration within a range from 2.0 mole percent to 100 mole percent of the acclerant with respect to 1 mole of the olefinic substrate. The main drawback of this invention is that the process involves the use of 2.0 to 100 mole percent acclerants.

R. A. Grey et al. in U.S. Pat. No. 6,194,591 (2001) disclosed an olefin epoxidation process using a titanium zeolite catalyst modified with Pt, Pd, or Cu compound. The main drawback of this invention is that the titanium silicate zeolite catalysts are acidic in nature they also catalyse the epoxide isomerization and/or epoxide ring opening, thereby reducing the selectivity for the formation of epoxide in the epoxidation process over these catalysts.

B. Zhou et al. in U.S. Pat. No. 6,534,661 (2003) discloses a bimetallic, primarily Pt and Pd noble metals supported on titanium containing silica support for the epoxidation of organic compounds such as propylene using hydrogen and oxygen at elevated pressure of 500-2000 psig. In this disclosure, the presence of Pt, Pd and Ti is essential for the epoxidation to occur. In addition, the reaction is carried out in gas/liquid phase but at elevated pressures and the catalyst is prepared by impregnation of reduced Pd and Pt containing solution (by hydrogen) on the titanium containing zeolite support. After filtration of the impregnated mass and drying, it is further reduced in hydrogen at 250-300° C. for 10-20 hours. The main drawback of this invention is that the process of this disclosure is expensive and complicated requiring heterogeneous deposition for formation of the catalyst, and elevated pressures during application for epoxidation V. R. Choudhary et al. in U.S. Pat. Publication No. 20050065355 (2005) discloses an invention relates to a process for the liquid phase epoxidation of a normally liquid olefinic compound to corresponding organic epoxide compound using aqueous or anhydrous organic hydroperoxide as an oxidizing agent in the presence of a supported nano-gold catalysts. The main drawback of this invention is that the process requires highly expensive nano-size gold particles as catalysts.

V. R. Choudhary et al. in U.S. Pat. Publication No. 20050113586 (2005) discloses an invention relates to a biphasic process for the epoxidation of an organic compound by organic hydroperoxide to the corresponding epoxide, using chromate or dichromate anions as the catalyst in aqueous medium. The main drawback of this invention is that the process requires organic hydroperoxide the mole ratio of 0.1 to 10 to olefinic compound.

Q. Tang, et al in Chem. Commun., 2004, 440-441 and Journal of Catalysis 230 (2005) 384-397, discloses the use of $Co^{2+}$ containing molecular sieves as catalysts for the epoxidation of styrene with molecular oxygen. They observed a maximum styrene conversion 45% with styrene oxide selectivity 65%. The main drawback of their process is that the styrene conversion is only 45% and styrene oxide selectivity is only 65%.

J. Liang et al in Catalysis Communications, 2004, 5, 665-669, describes $Fe^{2+}$-exchanged NaY zeolite and $Fe^{2+}$-containing compounds including $Fe_3(PO_4)_2$ and $Fe_3O_4$ as heterogeneous catalysts for the epoxidation of alkenes with molecular oxygen in the absence of a sacrificial reductant. A maximum styrene conversion 46.2% with styrene oxide selectivity 62.2% were observed in their reaction. The main drawback of their process is that styrene conversion is only 46.2% and styrene oxide selectivity is only 62.2%.

OBJECT OF THE INVENTION

The main object of the present invention is to provide a catalytic process for the epoxidation of styrene to styrene oxide with molecular oxygen, which obviates the drawbacks as detailed above.

Yet another object of the present invention is to provide an epoxidation catalyst based on synthetic zeolites.

Yet another object of the present invention is to provide an epoxidation catalyst uses molecular oxygen as the oxidant.

Yet another object of the present invention is to provide an epoxidation catalyst uses air as the oxidant.

Yet another object of the present invention is to provide an epoxidation process with increased styrene conversion and styrene oxide selectivity.

still another object of the present invention is to provide an epoxidation catalyst containing alkali and/or alkaline earth metal cationic promoters to increase the styrene oxide selectivity.

SUMMARY OF THE INVENTION

Accordingly, the present invention provides a process for the catalytic epoxidation of styrene with molecular oxygen using metal ion exchanged zeolite, which comprises reacting styrene with air or molecular oxygen in an organic solvent, in the presence of a zeolite based catalyst having the general formula $(CoO)_a \cdot (M_{2/n}O)_b \cdot (Al_2O_3)_c \cdot (SiO_2)_d \cdot wH_2O$, wherein the values of a varies from 8 to 48; b varies from 0 to 80 with 2a+b=c, w being the number of moles of water varies from 0 to 200 and M is alkali and/alkaline earth metal ion having valancy n, where n is +1 or +2, at a temperature in the range of 80-150° C., for a period of 3-6 hrs, separating the catalyst from the above said reaction mixture by known methods to obtain the desired product.

In an embodiment of the present invention the organic solvent used is selected from the group consisting of N,N-dimethylformamide (DMF), N,N-dimethylacetamide (DMA) and 1,4-dioxan.

In yet another embodiment the flow rate of air or molecular oxygen used is in the range of 3-5 ml per min.

In yet another embodiment the pressure of air or molecular oxygen used is in the range of 760 to 20000 Torr.

In yet another embodiment the zeolite catalyst used is dried at a temperature of 20-30° C. to retain the adsorbed water molecules inside the zeolite cavities.

In yet another embodiment the alkali and/or alkaline earth metal cationic promoter used in zeolite catalyst is selected from the group consisting of lithium, sodium, potassium, rubidium, cesium, magnesium, calcium, strontium, barium and a combination thereof.

In yet another embodiment the % conversion of styrene obtained is in the range of 70-99.9%.

In yet another embodiment the selectivity of the styrene oxide obtained is in the range of 60-90%.

DESCRIPTION OF THE INVENTION

In the present invention, we report a novel catalyst for the epoxidation of styrene to styrene oxide with molecular oxygen, having the chemical composition, $(Co)_x.(M_{2/n})_y Al_{88} Si_{104} O_{384} \cdot wH_2O$, where the values of x varies from 0 to 44, y from 0 to 88, w being the number of moles of water and M is a alkali or alkaline earth metal cation having valancy n. Zeolites, which are microporous crystalline alumna-silicates, are finding increased applications as catalysts for various chemical reactions. Zeolites have a three dimensional network of basic structural units consisting $SiO_4$ and $AlO_4$ tetrahedrons linked to each other by sharing apical oxygen atoms. Silicon and aluminium atoms lie in the centre of the tetrahedral. The resulting aluminosilicate structure, which is generally highly porous, possesses three-dimensional pores the access to which is through molecular sized windows. In a hydrated form, the preferred zeolites are generally represented by the following formula, $M_{2/n}O \cdot Al_2O_3 \cdot xSiO_2 \cdot wH_2O$, where M is a cation, which balances the electrovalence of the tetrahedral and is generally referred to as extra framework exchangeable cation, n represents the valancy of the cation and x and w represents the moles of $SiO_2$ and water respectively. The extra framework cations present in zeolites play significant role in determining their adsorption and catalytic properties. In particular, if co-ordinately unsaturated metal ions can be incorporated inside the zeolite cavities, novel adsorption and catalytic behaviour may be fashioned on the basis of coordination of guest molecules. Exchangeable transition metal ions in activated zeolites are generally co-ordinately unsaturated and readily form complexes with a variety of guest molecules. For applications, transition-metal ions are often introduced by ion-exchange; these can coordinate more selectively to guest molecules than filled-shell cations and often have easy access to other oxidation states, so their introduction into the zeolite allows new mechanisms for their function as sorbents and catalysts.

The attributes which makes the zeolites attractive as catalysts include, an unusually high thermal and hydrothermal stability, uniform pore structure, easy pore aperture modification and substantial catalytic activity. Furthermore, zeolites can be produced synthetically under relatively moderate hydrothermal conditions.

X-ray powder diffraction studies of various cobalt-exchanged zeolite at ambient temperature were carried out using PHILIPS X'pert MPD system in the 2θ range of 5-65 degrees using $CuK\alpha_1$ ($\lambda$=1.54056 Å). The diffraction patterns of the starting materials show that these are highly crystalline showing the reflections in the range 5 to 35 degrees typically of zeolites. The structure of the zeolite was retained during the cations exchange process. The X-ray powder pattern of various cobalt ion exchanged zeolites showed the loss of crystallinity during the cobalt ion exchange process. The X-ray diffraction at "2 theta" values 6.1, 10.0, 15.5, 20.1, 23.4, 26.7, 29.3, 30.5, 31.0 and 32.1 were used for comparison with the standard reference sample.

Surface area and pore size distribution of the various cobalt-exchanged zeolites were determined from the $N_2$ adsorption data at 77.35K. The equilibrium nitrogen adsorption at 77.35K was measured using Micromeritics ASAP 2010. The samples were activated at 100° C. under vacuum ($5\times10^3$ mmHg) for 12 hours before the $N_2$ sorption measurements. The surface areas of different catalyst samples were determined by applying BET and Langmuir equations in the $N_2$ adsorption data at 77.35K and the micropore area, micropore volume and external pore area by applying t-plot. The surface area of the zeolite samples increased on cobalt ion exchange. This is due to the decrease in the number of extra framework cations while replacing monovalent sodium ions with divalent cobalt ions. On replacing sodium ions with divalent cations such as cobalt, one $Co^{2+}$ replaces two $Na^+$ ions; therefore half the cations are present in the zeolite. The external surface area determined from the t-plot also increases with percentage of cobalt exchange. This can be explained in terms of the structural deformation occurred during the cation exchange process and/or vacuum dehydration at higher temperatures.

Diffuse Reflectance Spectroscopic (DRS) studies were carried out using Shimadzu UV-3101PC equipped with an integrating sphere. $BaSO_4$ was used as the reference material. The spectra were recorded at room temperature in the wavelength range of 200-750 nm. Diffuse reflectance spectroscopy (DRS) detects the d-d transitions of $Co^{2+}$ in the near infrared region and the $O \rightarrow Co^{2+}$ charge transfer transition in the ultraviolet region. In the hydrated pink sample, spectral minima appear around 530 nm in the visible region and 240 nm in the UV region. These absorptions are assigned to the transitions of the octahedral $[Co(H_2O)_6]^{2+}$ complex located in the super cages of the zeolites. The intensity of both the peaks at 530 nm and 240 nm increases correspondingly with the amount of cobalt exchange.

The zeolite in the powder form was used as the starting material. X-ray diffraction data showed that the starting material was highly crystalline. Cobalt cations were introduced into this highly crystalline zeolite by the cobalt ion exchange from aqueous solution. Typically, the zeolite was refluxed with a 0.01 to 1 M aqueous solution of the cobalt salt in the solid/liquid ratio 1:80 at 20 to 90° C. for 0.1 to 10 hours. The residue was filtered, washed with hot distilled water, until the washings were free from cobalt ions and dried at room temperature in air as specified in the examples. The extent of cobalt exchange was determined by the complexometric titration of the original solution and filtrate obtained after the ion exchange with EDTA using murexide indicator.

The sodium cations of the zeolites were replaced with various alkali and alkaline earth metal cations by ion exchanging with potassium, rubidium, cesium, magnesium, calcium, strontium and barium salt solution separately or in combination as explained in the examples. The ion exchange process was repeated several times to achieve the complete replacement of sodium ions with other alkali and alkaline earth metals. Cobalt cations were introduced into this highly crystalline zeolites by the cobalt ion exchange from aqueous solution. Typically, the zeolite was refluxed with a 0.01 to 1 M aqueous solution of the cobalt salt in the solid/liquid ratio 1:80 at 20 to, 90° C. for 0.1 to 10 hours. The residue was filtered, washed with hot distilled water, until the washings were free from nitrate ions and dried in air at room temperature. Zeolite samples having different amount of cobalt exchange were prepared by subjecting repeated ion exchange into the zeolite. The extent of cobalt exchange in zeolite was determined by the complexometric titration of the original solution and filtrate obtained after the ion exchange with EDTA using murexide indicator.

The cobalt ion exchanged zeolites dried at room temperature were used for the catalytic studies with out any further activation. The catalytic epoxidation reactions were carried out in liquid phase as a batch reaction at 100° C. Typically, a round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling $O_2$ at atmospheric pressure into the reaction mixture at the rate of 6-8 ml min$^1$. Tridecane was used as internal standard. The reaction mixture was magnetically stirred. After completing the reaction time, the catalyst was separated by centrifuging the reaction mixture and the liquid organic products were analysed with a gas chromatograph (Hewlett-Packard Model 6890, USA) having a flame ionisation detector and HP-5 capillary column (30 m length and 0.32 mm diameter, packed with silica-based supel cosil), programmed oven (temperature range 50-220° C.), and $N_2$ as carrier gas. Reaction kinetics was monitored by withdrawing small amount of the sample from the reaction flask at a time intervals of 30 minutes and analysing its composition by GC. Calibrations of GC peak areas of styrene and styrene oxide were carried out using solutions having known amounts of styrene and styrene oxide. The conversion was calculated on the basis of mole percent of styrene, the initial mole percent of styrene was divided by initial area percent (styrene peak area from GC) to get the response factor. The unreacted moles of styrene remained in the reaction mixture were calculated by multiplying response factor with the area percentage of the GC peak for styrene obtained after the reaction. The conversion, selectivity and turnover frequency (TOF) were calculated as follows:

$$\text{Conversion(mol \%)} = \frac{\text{(initial mol \%)} - \text{(final mol \%)}}{\text{initial mol \%}} \times 100$$

$$\text{Styrene Oxide Selectivity} = \frac{\text{GC peak area of Styrene Oxide}}{\text{GC peak area of all products}} \times 100$$

$$\text{TOF} = \frac{\text{No. of moles of Styrene oxide formed}}{\text{No. of moles of cobalt in the catalyst} \times \text{Reaction time}}$$

The spent catalyst was recovered from the reaction mixture by filtration and thoroughly washed with DMF, distilled water and then dried in air at room temperature.

The important inventive steps involved in the present invention are that the epoxidation catalyst, (i) is prepared by the cation exchange process using aqueous solution of cobalt salt in a temperature range of 20-90° C. and is used as the catalyst for the catalytic epoxidation reaction after drying at room temperatures obviating the high temperature activation (>350° C.) normally done for zeolite based catalysts, (ii) have alkali and/or alkaline earth metal cationic promoters for enhancing the styrene oxide selectivity and (iii) uses molecular oxygen/air for the catalytic epoxidation reactions at atmospheric pressure at 80-150° C.

The following examples are given by way of illustration and therefore should not be construed to limit the scope of the present invention.

EXAMPLE 1

The catalytic epoxidation reaction was carried out in liquid phase as a batch reaction at 100° C. using zeolite catalyst having the chemical composition $Na_{88}Al_{88}Si_{104}O_{384}.wH_2O$. A round bottom flask equipped with an efficient water condenser is kept in a constant temperature oil bath whose temperature was maintained at 100±2° C. 10 mmol styrene along with 20 ml N,N-dimethylformamide (DMF) and 200 mg zeolite were added to the flask. The reaction was started by bubbling $O_2$ at atmospheric pressure into the reaction mixture at the rate of 3-5 ml min$^{-1}$. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 2.5% styrene conversion with 56.5% styrene oxide selectivity was observed during the reaction.

EXAMPLE 2

Cobalt cations were introduced into this highly crystalline zeolite having the chemical composition $Na_{88}Al_{88}Si_{104}O_{384}.wH_2O$ by the cobalt ion exchange from aqueous solution. The zeolite was refluxed with 0.05M aqueous solution of the cobalt salt in the solid/liquid ratio 1:80 at 30±10° C. for 2 hours. The residue was filtered, washed with hot distilled water, until the washings were free from nitrate ions and dried in air at room temperature. The extent of cobalt exchange in zeolite was determined by the complexometric titration of the original solution and filtrate obtained after the ion exchange with EDTA using murexide indicator. The cobalt ion exchanged zeolite (NaCoX 10) dried at room temperature was used for the catalytic studies with out any further activation. The catalytic epoxidation reactions were carried out in liquid phase as a batch reaction at 100° C. using NaCoX 10. A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling $O_2$ at atmospheric pressure into the reaction mixture at the rate of 3-5 ml min$^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 66.0% styrene conversion with 66.9% styrene oxide selectivity was observed during the reaction.

EXAMPLE 3

The cobalt exchanged zeolite obtained in the Example-2 (NaCoX 10) was further refluxed with 0.05M aqueous solution of the cobalt salt in the solid/liquid ratio 1:80 at 40±10° for 1 hour. The residue was filtered, washed with hot distilled water, until the washings were free from nitrate ions and dried in air at room temperature. The extent of cobalt exchange in zeolite was determined by the complexometric titration of the original solution and filtrate obtained after the ion exchange with EDTA using murexide indicator. The cobalt ion exchanged zeolite (NaCoX 19) dried at room temperature was used for the catalytic studies with out any further activation. The catalytic epoxidation reactions were carried out in liquid phase as a batch reaction at 100° C. using NaCoX 19. A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling $O_2$ at atmospheric pressure into the reaction mixture at the rate of 3-5 ml min$^{-1}$.

Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 77.9% styrene conversion with 67.5% styrene oxide selectivity was observed during the reaction.

EXAMPLE 4

The cobalt exchanged zeolite obtained in the Example-3 (NaCoX 19) was further refluxed with 0.05M aqueous solution of the cobalt salt in the solid/liquid ratio 1:80 at 50±10° C. for 4 hours. The residue was filtered, washed with hot distilled water, until the washings were free from nitrate ions and dried in air at room temperature. The extent of cobalt exchange in zeolite was determined by the complexometric titration of the original solution and filtrate obtained after the ion exchange with EDTA using murexide indicator. The cobalt ion exchanged zeolite (NaCoX 34) dried at room temperature was used for the catalytic studies with out any further activation. The catalytic epoxidation reactions were carried out in liquid phase as a batch reaction at 100° C. using NaCoX 34. A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling $O_2$ at atmospheric pressure into the reaction mixture at the rate of 3-5 ml min$^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 87.6% styrene conversion with 65.1% styrene oxide selectivity was observed during the reaction.

EXAMPLE 5

The cobalt exchanged zeolite obtained in the Example-4 (NaCoX 34) was further refluxed with 0.05M aqueous solution of the cobalt salt in the solid/liquid ratio 1:80 at 60±10° C. for 4 hours. The residue was filtered, washed with hot distilled water, until the washings were free from nitrate ions and dried in air at room temperature. The extent of cobalt exchange in zeolite was determined by the complexometric titration of the original solution and filtrate obtained after the ion exchange with EDTA using murexide indicator. The cobalt ion exchanged zeolite (NaCoX 69) dried at room temperature was used for the catalytic studies with out any further activation. The catalytic epoxidation reactions were carried out in liquid phase as a batch reaction at 100° C. using NaCoX 69. A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling $O_2$ at atmospheric pressure into the reaction mixture at the rate of 3-5 ml min$^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 97.2% styrene conversion with 67.7% styrene oxide selectivity was observed during the reaction.

EXAMPLE 6

The cobalt exchanged zeolite obtained in the Example-5 (NaCoX 69) was further refluxed with 0.05M aqueous solution of the cobalt salt in the solid/liquid ratio 1:80 at 70±10° C. for 4 hours. The residue was filtered, washed with hot distilled water, until the washings were free from nitrate ions and dried in air at room temperature. The extent of cobalt exchange in zeolite was determined by the complexometric titration of the original solution and filtrate obtained after the ion exchange with EDTA using murexide indicator. The cobalt ion exchanged zeolite (NaCoX 81) dried at room temperature was used for the catalytic studies with out any further activation. The catalytic epoxidation reactions were carried out in liquid phase as a batch reaction at 100° C. using NaCoX 81. A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling $O_2$ at atmospheric pressure into the reaction mixture at the rate of 3-5 ml min$^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 97.9% styrene conversion with 68.0% styrene oxide selectivity was observed during the reaction.

EXAMPLE 7

The cobalt exchanged zeolite obtained in the Example-6 (NaCoX 81) was further refluxed with 0.05M aqueous solution of the cobalt salt in the solid/liquid ratio 1:80 at 80±10° C. for 4 hours. The residue was filtered, washed with hot distilled water, until the washings were free from nitrate ions and dried in air at room temperature. The extent of cobalt exchange in zeolite was determined by the complexometric titration of the original solution and filtrate obtained after the ion exchange with EDTA using murexide indicator. The cobalt ion exchanged zeolite (NaCoX 92) dried at room temperature was used for the catalytic studies with out any further activation. The catalytic epoxidation reactions were carried out in liquid phase as a batch reaction at 100° C. using NaCoX 92. A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling $O_2$ at atmospheric pressure into the reaction mixture at the rate of 3-5 ml min$^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 98.4% styrene conversion with 66.4% styrene oxide selectivity was observed during the reaction.

EXAMPLE 8

The catalytic epoxidation reactions were carried out in liquid phase as a batch reaction at 100° C. using the catalyst prepared by the method described in example 7 (NaCoX 92). A round bottom flask equipped with an efficient water condenser is kept in a constant temperature oil bath whose temperature was maintained at 100±2° C. N,N-dimethylformamide (DMF) was dried by the addition of calcium hydride followed by the vacuum distillation at 60° C. The catalyst was dried at 80° C. under vacuum for 24 hours. 10 mmol styrene along with 20 ml dried DMF and 200 mg dried catalyst were added to the flask. The reaction was started by bubbling $O_2$ at atmospheric pressure into the reaction mixture at the rate of 3-5 ml min$^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 41.8% styrene conversion with 67.8% styrene oxide selectivity was observed during the reaction.

EXAMPLE 9

The catalytic epoxidation reactions were carried out in liquid phase as a batch reaction at 100° C. using the catalyst prepared by the method described in example 7 (NaCoX 92). A round bottom flask equipped with an efficient water condenser is kept in a constant temperature oil bath whose temperature was maintained at 100±2° C. N,N-dimethylformamide (DMF) was dried by the addition of calcium hydride followed by the vacuum distillation at 60° C. The catalyst dried at room temperature was used for the catalytic studies with out any further activation. 10 mmol styrene along with 20 ml dried DMF and 200 mg catalyst were added to the flask. The reaction was started by bubbling $O_2$ at atmospheric pressure into the reaction mixture at the rate of 3-5 ml min$^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 64.9% styrene conversion with 66.9% styrene oxide selectivity was observed during the reaction.

EXAMPLE 10

The catalytic epoxidation reactions were carried out in liquid phase as a batch reaction at 100° C. using the catalyst prepared by the method described in example 7 (NaCoX 92). A round bottom flask equipped with an efficient water condenser is kept in a constant temperature oil bath whose temperature was maintained at 100±2° C. N,N-dimethylformamide (DMF) was dried by the addition of calcium hydride followed by the vacuum distillation at 60° C. The catalyst was dried at 80° C. under vacuum for 24 hours. 10 mmol styrene along with 20 ml dried DMF, 200 mg dried catalyst and 1.0 ml distilled water were added to the flask. The reaction was started by bubbling $O_2$ at atmospheric pressure into the reaction mixture at the rate of 3-5 ml min$^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 98.4% styrene conversion with 66.4% styrene oxide selectivity was observed during the reaction.

EXAMPLE 11

The catalytic epoxidation reactions were carried out in liquid phase as a batch reaction at 100° C. using the catalyst prepared by the method described in example 7 (NaCoX 92). A round bottom flask equipped with an efficient water condenser is kept in a constant temperature oil bath whose temperature was maintained at 100±2° C. 10 mmol styrene along with 20 ml N,N-dimethylformamide (DMF), 200 mg catalyst and 1 ml distilled water were added to the flask. The reaction was started by bubbling $O_2$ at atmospheric pressure into the reaction mixture at the rate of 3-5 ml min$^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 99.9% styrene conversion with 65.3% styrene oxide selectivity was observed during the reaction.

EXAMPLE 12

The cobalt exchanged zeolite obtained in the Example-7 (NaCoX 92) was further refluxed with 0.05M aqueous solution of the cobalt salt in the solid/liquid ratio 1:80 at 80±10° C. for 4 hours. The residue was filtered, washed with hot distilled water, until the washings were free from nitrate ions and dried in air at room temperature. The extent of cobalt exchange in zeolite was determined by the complexometric titration of the original solution and filtrate obtained after the ion exchange with EDTA using murexide indicator. The cobalt ion exchanged zeolite (NaCoX 96) dried at room temperature were used for the catalytic studies with out any further activation. The catalytic epoxidation reactions were carried out in liquid phase as a batch reaction at 100° C. using NaCoX 96. A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling $O_2$ at atmospheric pressure into the reaction mixture at the rate of 3-5 ml min$^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 99.8% styrene conversion with 66.9% styrene oxide selectivity was observed during the reaction.

EXAMPLE 13

The sodium cations of the zeolite having the chemical composition $Na_{88}Al_{88}Si_{104}O_{384}.wH_2O$ were replaced with potassium cations by cation exchanging with 1 M KCl solution at 80±10° C. The cation exchange process was repeated four times to achieve the complete replacement of sodium ions with potassium ions. Cobalt cations were introduced into this potassium form of zeolite by the cobalt ion exchange from aqueous solution. The potassium form of the zeolite was refluxed with 0.05M aqueous solution of the cobalt salt in the solid/liquid ratio 1:80 at 50±10° C. for 2 hours. The residue was filtered, washed with hot distilled water, until the washings were free from nitrate ions and dried in air at room temperature. The extent of cobalt exchange in zeolite was determined by the complexometric titration of the original solution and filtrate obtained after the ion exchange with EDTA using murexide indicator. The cobalt ion exchanged zeolite (KCoX 19) obtained was dried at room temperature and used for the catalytic studies without any further activation. The catalytic epoxidation reactions were carried out in liquid phase as a batch reaction at 100° C. using KCoX 19. A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling $O_2$ at atmospheric pressure into the reaction mixture at the rate of 3-5 ml min$^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 98.7% styrene conversion with 71.3% styrene oxide selectivity was observed during the reaction.

EXAMPLE 14

The sodium cations of the zeolite having the chemical composition $Na_{88}Al_{88}Se_{104}O_{384}.wH_2O$ were replaced with rubidium cations by cation exchanging with 1 M RbCl solution at 80±10° C. The cation exchange process was repeated four times to achieve the complete replacement of sodium ions with rubidium ions. Cobalt cations were introduced into this rubidium form of zeolite by the cobalt ion exchange from aqueous solution. The rubidium form of the zeolite was refluxed with 0.05M aqueous solution of the cobalt salt in the solid/liquid ratio 1:80 at 50±10° C. for 2 hours. The residue was filtered, washed with hot distilled water, until the washings were free from nitrate ions and dried in air at room temperature. The extent of cobalt exchange in zeolite was determined by the complexometric titration of the original solution and filtrate obtained after the ion exchange with EDTA using murexide indicator. The cobalt ion exchanged zeolite (RbCoX 22) obtained was dried at room temperature and used for the catalytic studies with out any further activation. The catalytic epoxidation reactions were carried out in liquid phase as a batch reaction at 100° C. using RbCoX 22. A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling $O_2$ at atmospheric pressure into the reaction mixture at the rate of 3-5 ml min$^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 98.6% styrene conversion with 71.8% styrene oxide selectivity was observed during the reaction.

EXAMPLE 15

The sodium cations of the zeolite having the chemical composition $Na_{88}Al_{88}Si_{104}O_{384}.wH_2O$ were replaced with cesium cations by cation exchanging with 1 M CsCl solution at 80±10° C. The cation exchange process was repeated four times to achieve the complete replacement of sodium ions with cesium ions. Cobalt cations were introduced into this cesium form of zeolite by the cobalt ion exchange from aqueous solution. The cesium exchanged zeolite was refluxed with 0.05M aqueous solution of the cobalt salt in the solid/liquid ratio 1:80 at 50±10° C. for 2 hours. The residue was filtered, washed with hot distilled water, until the washings were free from nitrate ions and dried in air at room temperature. The extent of cobalt exchange in zeolite was determined by the complexometric titration of the original solution and filtrate obtained after the ion exchange with EDTA using murexide indicator. The cobalt ion exchanged zeolite (CsCoX 20) obtained was dried at room temperature and used for the catalytic studies with out any further activation. The catalytic epoxidation reactions were carried out in liquid phase as a batch reaction at 100° C. using CsCoX 20. A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling $O_2$ at atmospheric pressure into the reaction mixture at the rate of 3-5 ml min$^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 99.8% styrene conversion with 76.6% styrene oxide selectivity was observed during the reaction.

EXAMPLE 16

The sodium cations of the zeolite having the chemical composition $Na_{88}Al_{88}Si_{104}O_{384}.wH_2O$ were replaced with magnesium cations by cation exchanging with 1 M $MgCl_2$ solution at 80±10° C. The cation exchange process was repeated four times to achieve the complete replacement of sodium ions with magnesium ions. Cobalt cations were introduced into this magnesium form of zeolite by the cobalt ion exchange from aqueous solution. The magnesium exchanged zeolite was refluxed with 0.05M aqueous solution of the cobalt salt in the solid/liquid ratio 1:80 at 60±10° C. for 2 hours. The residue was filtered, washed with hot distilled water, until the washings were free from nitrate ions and dried in air at room temperature. The extent of cobalt exchange in zeolite was determined by the complexometric titration of the original solution and filtrate obtained after the ion exchange with EDTA using murexide indicator. The cobalt ion exchanged zeolite (MgCoX 22) obtained was dried at room temperature and used for the catalytic studies with out any further activation. The catalytic epoxidation reactions were carried out in liquid phase as a batch reaction at 100° C. using MgCoX 22. A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling $O_2$ at atmospheric pressure into the reaction mixture at the rate of 3-5 ml min$^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 99.5% styrene conversion with 74.6% styrene oxide selectivity was observed during the reaction.

EXAMPLE 17

The sodium cations of the zeolite having the chemical composition $Na_{88}Al_{88}Si_{104}O_{384}.wH_2O$ were replaced with calcium cations by cation exchanging with 1 M $CaCl_2$ solution at 80±10° C. The cation exchange process was repeated four times to achieve the complete replacement of sodium ions with calcium ions. Cobalt cations were introduced into this calcium form of zeolite by the cobalt ion exchange from aqueous solution. The calcium exchanged zeolite thus obtained was refluxed with 0.05M aqueous solution of the cobalt salt in the solid/liquid ratio 1:80 at 60±10° C. for 2 hours. The residue was filtered, washed with hot distilled water, until the washings were free from nitrate ions and dried in air at room temperature. The extent of cobalt exchange in zeolite was determined by the complexometric titration of the original solution and filtrate obtained after the ion exchange with EDTA using murexide indicator. The cobalt ion exchanged zeolite (CaCoX 19) thus obtained was dried at room temperature were used for the catalytic studies with out any further activation. The catalytic epoxidation reactions were carried out in liquid phase as a batch reaction at 100° C. using CaCoX 19. A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling $O_2$ at atmospheric pressure into the reaction mixture at the rate of 3-5 ml min$^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 99.8% styrene conversion with 82.9% styrene oxide selectivity was observed during the reaction.

EXAMPLE 18

The sodium cations of the zeolite having the chemical composition $Na_{88}Al_{88}Si_{104}O_{384}.wH_2O$ were replaced with strontium cations by cation exchanging with 1 M $Sr(NO_3)_2$ solution at 80±10° C. The cation exchange process was repeated four times to achieve the complete replacement of sodium ions with strontium ions. Cobalt cations were introduced into this strontium form of zeolite by the cobalt ion exchange from aqueous solution. The strontium exchanged zeolite was refluxed with 0.05M aqueous solution of the cobalt salt in the solid/liquid ratio 1:80 at 60±10° C. for 2 hours. The residue was filtered, washed with hot distilled water, until the washings were free from nitrate ions and dried in air at room temperature. The extent of cobalt exchange in zeolite was determined by the complexometric titration of the original solution and filtrate obtained after the ion exchange with EDTA using murexide indicator. The cobalt ion exchanged zeolite (SrCoX 18) thus obtained was dried at room temperature and used for the catalytic studies with out any further activation. The catalytic epoxidation reactions were carried out in liquid phase as a batch reaction at 100° C. using SrCoX 18. A round bottom flask equipped with an efficient water condenser is kept in a constant temperature oil bath whose temperature was maintained at 100±2° C. 10 mmol styrene along with 20 ml N,N-dimethyl formamide (DMF) and 200 mg catalyst were added to the flask. The reaction was started by bubbling $O_2$ at atmospheric pressure into the reaction mixture at the rate of 3-5 ml min$^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 99.9% styrene conversion with 85.1% styrene oxide selectivity was observed during the reaction.

EXAMPLE 19

The sodium cations of the zeolite having the chemical composition $Na_{88}Al_{88}Si_{104}O_{384}.wH_2O$ were replaced with barium cations by cation exchanging with 1 M $BaCl_2$ solution at 80±10° C. The cation exchange process was repeated four times to achieve the complete replacement of sodium ions with barium ions. Cobalt cations were introduced into this barium form of zeolite by the cobalt ion exchange from aqueous solution. The barium exchanged zeolite was refluxed with 0.05M aqueous solution of the cobalt salt in the solid/liquid ratio 1:80 at 60±10° C. for 2 hours. The residue was filtered, washed with hot distilled water, until the washings were free from nitrate ions and dried in air at room temperature. The extent of cobalt exchange in zeolite was determined by the complexometric titration of the original solution and filtrate obtained after the ion exchange with EDTA using murexide indicator. The cobalt ion exchanged zeolite (BaCoX 15) thus obtained was dried at room temperature and used for the catalytic studies with out any further activation. The catalytic epoxidation reactions were carried out in liquid phase as a batch reaction at 100° C. using BaCoX 15. A round bottom flask equipped with an efficient water condenser is kept in a constant temperature oil bath whose temperature was maintained at 100±2° C. 10 mmol styrene along with 20 ml N,N-dimethyl formamide (DMF) and 200 mg catalyst were added to the flask. The reaction was started by bubbling $O_2$ at atmospheric pressure into the reaction mixture at the rate of 3-5 ml min$^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 99.9% styrene conversion with 82.6% styrene oxide selectivity was observed during the reaction.

EXAMPLE 20

The sodium cations of the zeolite having the chemical composition $Na_{88}Al^{88}Si^{104}O^{384}.wH_2O$ were replaced with barium cations by cation exchanging with 1 M $BaCl_2$ solution at 80±10° C. The cation exchange process was repeated four times to achieve the complete replacement of sodium ions with barium ions. The barium ion exchanged zeolite was them refluxed with 1 M CsCl solution at 80±10° C. for replacing some of the barium cations with cesium cations. Cobalt cations were introduced into this barium and cesium form of zeolite by the cobalt ion exchange from aqueous solution. The zeolite was refluxed with 0.05M aqueous solution of the cobalt salt in the solid/liquid ratio 1:80 at 60±10° C. for 2 hours. The residue was filtered, washed with hot distilled water, until the washings were free from nitrate ions and dried in air at room temperature. The extent of cobalt exchange in zeolite was determined by the complexometric titration of the original solution and filtrate obtained after the ion exchange with EDTA using murexide indicator. The cobalt ion exchanged zeolite (CsBaCoX 20) thus obtained was dried at room temperature and used for the catalytic studies with out any further activation. The catalytic epoxidation reactions were carried out in liquid phase as a batch reaction at 100° C. using CsBaCoX 20. A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling $O_2$ at atmospheric pressure into the reaction mixture at the rate of 3-5 ml min$^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 99.4% styrene conversion with 80.4% styrene oxide selectivity was observed during the reaction.

EXAMPLE 21

The sodium cations of the zeolite having the chemical composition $Na_{88}Al_{88}Si_{104}O_{384}.wH_2O$ were replaced with potassium cations by cation exchanging with 1 M KCl solution at 80±10° C. The cation exchange process was repeated four times to achieve the complete replacement of sodium ions with potassium ions. Some of the potassium cations of the zeolite were replaced with barium cations by cation exchanging with 1 M $BaCl_2$ solution at 80±10° C. Cobalt cations were introduced into this barium form of zeolite by the cobalt ion exchange from aqueous solution. The zeolite was refluxed with 0.05M aqueous solution of the cobalt salt in the solid/liquid ratio 1:80 at 60±10° C. for 2 hours. The residue was filtered, washed with hot distilled water, until the washings were free from nitrate ions and dried in air at room temperature. The extent of cobalt exchange in zeolite was determined by the complexometric titration of the original solution and filtrate obtained after the ion exchange with EDTA using murexide indicator. The cobalt ion exchanged zeolite (KBaCoX 21) thus obtained was dried at room temperature and used for the catalytic studies with out any further activation. The catalytic epoxidation reactions were carried out in liquid phase as a batch reaction at 100° C. using KBaCoX 21. A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling $O_2$ at atmospheric pressure into the reaction mixture at the rate of 3-5 ml min$^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 99.8% styrene conversion with 83.1% styrene oxide selectivity was observed during the reaction.

EXAMPLE 22

The sodium cations of the zeolite having the chemical composition $Na_{88}Al_{88}Si_{104}O_{384}.wH_2O$ were replaced with potassium cations by cation exchanging with 1 M KCl solution at 80±10° C. The cation exchange process was repeated four times to achieve the complete replacement of sodium ions with potassium ions. Some of the potassium cations of the zeolite were replaced with strontium cations by cation exchanging with 1 M $Sr(NO_3)_2$ solution at 80±10° C. Cobalt cations were introduced into this strontium form of zeolite by the cobalt ion exchange from aqueous solution. The zeolite was refluxed with 0.05M aqueous solution of the cobalt salt in the solid/liquid ratio 1:80 at 60±10° C. for 2 hours. The residue was filtered, washed with hot distilled water, until the washings were free from nitrate ions and dried in air at room temperature. The extent of cobalt exchange in zeolite was determined by the complexometric titration of the original solution and filtrate obtained after the ion exchange with EDTA using murexide indicator. The cobalt ion exchanged zeolite (KSrCoX 20) thus obtained was dried at room temperature and used for the catalytic studies with out any further activation. The catalytic epoxidation reactions were carried out in liquid phase as a batch reaction at 100° C. using KSrCoX 20. A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling $O_2$ at atmospheric pressure into the reaction mixture at the rate of 3-5 ml min$^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 99.6% styrene conversion with 81.0% styrene oxide selectivity was observed during the reaction.

EXAMPLE 23

The cobalt ion exchanged zeolite having the chemical composition $Na_{88}Al_{88}Si_{104}O_{384}.wH_2O$ prepared by the method described in example 6 (NaCoX 81) was used for the catalytic studies using air. The catalytic epoxidation reactions were carried out in liquid phase as a batch reaction at 100° C. using (NaCoX 81). A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling atmospheric air into the reaction mixture at the rate of 5-7 ml min$^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 99.2% styrene conversion with 66.4% styrene oxide selectivity was observed during the reaction.

EXAMPLE 24

The cobalt exchanged zeolite having the chemical composition $Na_{88}Al_{88}Si_{104}O_{384}.wH_2O$ prepared by the method described in the Example-7 (NaCoX 92) was used for the catalytic epoxidation reaction at 100° C. using atmospheric air as the molecular oxygen source. A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling atmospheric air into the reaction mixture at the rate of 5-7 ml $min^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 99.4% styrene conversion with 65.5% styrene oxide selectivity was observed during the reaction.

EXAMPLE 25

The catalytic epoxidation reactions were carried out in liquid phase as a batch reaction at 100° C. using the catalyst prepared by the method described in Example (KCoX 19) and atmospheric air as molecular oxygen source. A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling atmospheric air into the reaction mixture at the rate of 5-7 ml $min^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 98.7% styrene conversion with 71.3% styrene oxide selectivity was observed during the reaction.

EXAMPLE 26

The catalytic epoxidation reactions were carried out in liquid phase as a batch reaction at 100° C. using the catalyst prepared by the method described in Example 15 (CsCoX 20) and atmospheric air as molecular oxygen source. A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling atmospheric air into the reaction mixture at the rate of 5-7 ml $min^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 99.8% styrene conversion with 76.9% styrene oxide selectivity was observed during the reaction.

EXAMPLE 27

The catalytic epoxidation reactions were carried out in liquid phase as a batch reaction at 100° C. using the catalyst prepared by the method described in Example 17 (CaCoX 19) and atmospheric air as molecular oxygen source. A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling atmospheric air into the reaction mixture at the rate of 5-7 ml $min^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 99.8% styrene conversion with 83.8% styrene oxide selectivity was observed during the reaction.

EXAMPLE 28

The catalytic epoxidation reactions were carried out in liquid phase as a batch reaction at 100° C. using the catalyst prepared by the method described in Example 18(SrCoX 18) and atmospheric air as molecular oxygen source. A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling atmospheric air into the reaction mixture at the rate of 5-7 ml $min^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 99.9% styrene conversion with 85.9% styrene oxide selectivity was observed during the reaction.

EXAMPLE 29

The catalytic epoxidation reactions were carried out in liquid phase as a batch reaction at 100° C. using the catalyst prepared by the method described in Example 19(BaCoX 15) and atmospheric air as molecular oxygen source. A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling atmospheric air into the reaction mixture at the rate of 5-7 ml $min^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 99.9% styrene conversion with 83.9% styrene oxide selectivity was observed during the reaction.

EXAMPLE 30

The cobalt ion exchanged zeolite (NaCoX 92) catalyst used for the catalytic epoxidation of styrene to styrene oxide in Example 7 was recovered by centrifuging and was washed with DMF, followed by distilled water and dried at room temperature was used for the catalytic epoxidation reactions were carried out in liquid phase as a batch reaction at 100° C., with out any further activation. A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling $O_2$ at atmospheric pressure into the reaction mixture at the rate of 3-5 ml min$^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 98.4% styrene conversion with 66.4% styrene oxide selectivity was observed during the reaction.

EXAMPLE 31

The cobalt ion exchanged zeolite (NaCoX 92) catalyst used for the catalytic epoxidation of styrene to styrene oxide in Example 30 was recovered by centrifuging and was washed with DMF, followed by distilled water and dried at room temperature was used for the catalytic epoxidation reactions were carried out in liquid phase as a batch reaction at 100° C., with out any further activation. A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling $O_2$ at atmospheric pressure into the reaction mixture at the rate of 3-5 ml min$^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 99.3% styrene conversion with 67.2% styrene oxide selectivity was observed during the reaction.

EXAMPLE 32

The cobalt ion exchanged zeolite (NaCoX 92) catalyst used for the catalytic epoxidation of styrene to styrene oxide in Example 31 was recovered by centrifuging and was washed with DMF, followed by distilled water and dried at room temperature was used for the catalytic epoxidation reactions were carried out in liquid phase as a batch reaction at 100° C., with out any further activation. A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling $O_2$ at atmospheric pressure into the reaction mixture at the rate of 3-5 ml min$^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 99.2% styrene conversion with 66.9% styrene oxide selectivity was observed during the reaction.

EXAMPLE 33

The cobalt ion exchanged zeolite (SrCoX 18) catalyst used for the catalytic epoxidation of styrene to styrene oxide in Example 18 was recovered by centrifuging and was washed with DMF, followed by distilled water and dried at room temperature was used for the catalytic epoxidation reactions were carried out in liquid phase as a batch reaction at 100° C., with out any further activation. A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling $O_2$ at atmospheric pressure into the reaction mixture at the rate of 3-5 ml min$^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 99.9% styrene conversion with 85.1% styrene oxide selectivity was observed during the reaction.

EXAMPLE 34

The cobalt ion exchanged zeolite (SrCoX 18) catalyst used for the catalytic epoxidation of styrene to styrene oxide in Example 33 was recovered by centrifuging and was washed with DMF, followed by distilled water and dried at room temperature was used for the catalytic epoxidation reactions were carried out in liquid phase as a batch reaction at 100° C., with out any further activation. A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling $O_2$ at atmospheric pressure into the reaction mixture at the rate of 3-5 ml min$^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 99.9% styrene conversion with 85.3% styrene oxide selectivity was observed during the reaction.

EXAMPLE 35

The cobalt ion exchanged zeolite (BaCoX 92) catalyst used for the catalytic epoxidation of styrene to styrene oxide in Example 19 was recovered by centrifuging and was washed with DMF, followed by distilled water and dried at room temperature was used for the catalytic epoxidation reactions were carried out in liquid phase as a batch reaction at 100° C., with out any further activation. A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling $O_2$ at atmospheric pressure into the reaction mixture at the rate of 3-5 ml min$^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 99.9% styrene conversion with 82.6% styrene oxide selectivity was observed during the reaction.

EXAMPLE 36

The cobalt ion exchanged zeolite (NaCoX 92) catalyst used for the catalytic epoxidation of styrene to styrene oxide in Example 7 was recovered by centrifuging and was washed with DMF, followed by distilled water and dried at room temperature was used for the catalytic epoxidation reactions were carried out in liquid phase as a batch reaction at 100° C., with out any further activation. A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling $O_2$ at atmospheric pressure into the reaction mixture at the rate of 3-5 ml min$^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 99.8% styrene conversion with 82.9% styrene oxide selectivity was observed during the reaction.

EXAMPLE 37

Cobalt cations were introduced into this highly crystalline zeolite having the chemical composition $Na_{30}Al_{30}Si_{160}O_{384}.wH_2O$ by the cobalt ion exchange from aqueous solution. The zeolite was refluxed with 0.05M aqueous solution of the cobalt salt in the solid/liquid ratio 1:80 at 80±10° C. for 2 hours. The residue was filtered, washed with hot distilled water, until the washings were free from nitrate ions and dried in air at room temperature. The extent of cobalt exchange in zeolite was determined by the complexometric titration of the original solution and filtrate obtained after the ion exchange with EDTA using murexide indicator. The cobalt ion exchanged zeolite (NaCoY) dried at room temperature was used for the catalytic studies with out any further activation. The catalytic epoxidation reactions were carried out in liquid phase as a batch reaction at 100° C. using NaCoY. A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling $O_2$ at atmospheric pressure into the reaction mixture at the rate of 3-5 ml min$^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 89.0% styrene conversion with 63.1% styrene oxide selectivity was observed during the reaction.

EXAMPLE 38

Cobalt cations were introduced into this highly crystalline zeolite having the chemical composition $Na_8Al_8Si_{40}O_{96}.wH_2O$ by the cobalt ion exchange from aqueous solution. The zeolite was refluxed with 0.05M aqueous solution of the cobalt salt in the solid/liquid ratio 1:80 at 80±10° C. for 2 hours. The residue was filtered, washed with hot distilled water, until the washings were free from nitrate ions and dried in air at room temperature. The extent of cobalt exchange in zeolite was determined by the complexometric titration of the original solution and filtrate obtained after the ion exchange with EDTA using murexide indicator. The cobalt ion exchanged zeolite (NaCoMor060) dried at room temperature was used for the catalytic studies with out any further activation. The catalytic epoxidation reactions were carried out in liquid phase as a batch reaction at 100° C. using NaCoMor060. A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling $O_2$ at atmospheric pressure into the reaction mixture at the rate of 3-5 ml min$^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 92.0% styrene conversion with 61.0% styrene oxide selectivity was observed during the reaction.

EXAMPLE 39

Cobalt cations were introduced into this highly crystalline zeolite having the chemical composition $Na_{2.5}Al_{2.5}Si_{61.5}O_{128}.wH_2O$ by the cobalt ion exchange from aqueous solution The zeolite was refluxed with 0.05M aqueous solution of the cobalt salt in the solid/liquid ratio 1:80 at 80±10° C. for 2 hours. The residue was filtered, washed with hot distilled water, until the washings were free from nitrate ions and dried in air at room temperature. The extent of cobalt exchange in zeolite was determined by the complexometric titration of the original solution and filtrate obtained after the ion exchange with EDTA using murexide indicator. The cobalt ion exchanged zeolite (NaCoBEA) dried at room temperature was used for the catalytic studies with out any further activation. The catalytic epoxidation reactions were carried out in liquid phase as a batch reaction at 100° C. using NaCoBEA. A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling $O_2$ at atmospheric pressure into the reaction mixture at the rate of 3-5 ml min$^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 86.0% styrene conversion with 56.2% styrene oxide selectivity was observed during the reaction.

EXAMPLE 40

Cobalt cations were introduced into this highly crystalline zeolite having the chemical composition $K_9Al_9Si_{27}O_{72}.wH_2O$ by the cobalt ion exchange from aqueous solution. The zeolite was refluxed with 0.05M aqueous solution of the cobalt salt in the solid/liquid ratio 1:80 at 80±10° C. for 2 hours. The residue was filtered, washed with hot distilled water, until the washings were free from nitrate ions and dried in air at room temperature. The extent of cobalt exchange in zeolite was determined by the complexometric titration of the original solution and filtrate obtained after the ion exchange with EDTA using murexide indicator. The cobalt ion exchanged zeolite (KCoL) dried at room temperature was used for the catalytic studies with out any further activation. The catalytic epoxidation reactions were carried out in liquid phase as a batch reaction at 100° C. using KCoL. A round bottom flask equipped with an efficient water condenser is kept in a constant temperature oil bath whose temperature was maintained at 100±2° C. 10 mmol styrene along with 20 ml N,N-dimethylformamide (DMF) and 200 mg catalyst were added to the flask. The reaction was started by bubbling $O_2$ at atmospheric pressure into the reaction mixture at the rate of 3-5 ml $min^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 80.1% styrene conversion with 51.9% styrene oxide selectivity was observed during the reaction.

EXAMPLE 41

The catalytic epoxidation reactions were carried out in liquid phase as a batch reaction at 100° C. using the catalyst prepared by the method described in Example 17 (CaCoX 19). A round bottom flask equipped with an efficient water condenser is kept in a constant temperature oil bath whose temperature was maintained at 100±2° C. 10 mmol styrene along with 20 ml 1,4-dioxan and 200 mg catalyst were added to the flask. The reaction was started by bubbling oxygen into the reaction mixture at the rate of 3-5 ml $min^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 93.6% styrene conversion with 73.1% styrene oxide selectivity was observed during the reaction.

EXAMPLE 42

The catalytic epoxidation reactions were carried out in liquid phase as a batch reaction at 100° C. using the catalyst prepared by the method described in Example 17 (CaCoX 19). A round bottom flask equipped with an efficient water condenser is kept in a constant temperature oil bath whose temperature was maintained at 100±2° C. 10 mmol styrene along with 20 ml N,N-dimethylacetamide (DMA) and 200 mg catalyst were added to the flask. The reaction was started by bubbling oxygen into the reaction mixture at the rate of 3-5 ml $min^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 99.1% styrene conversion with 85.9% styrene oxide selectivity was observed during the reaction.

EXAMPLE 43

The catalytic epoxidation reactions were carried out in liquid phase as a batch reaction at 100° C. using the catalyst prepared by the method described in Example 19(BaCoX 15). A round bottom flask equipped with an efficient water condenser is kept in a constant temperature oil bath whose temperature was maintained at 80±2° C. 10 mmol styrene along with 20 ml N,N-dimethylformamide (DMF) and 200 mg catalyst were added to the flask. The reaction was started by bubbling oxygen into the reaction mixture at the rate of 3-5 ml $min^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 39.9% styrene conversion with 84.9% styrene oxide selectivity was observed during the reaction.

EXAMPLE 44

The catalytic epoxidation reactions were carried out in liquid phase as a batch reaction at 100° C. using the catalyst prepared by the method described in Example 19(BaCoX 15). A round bottom flask equipped with an efficient water condenser is kept in a constant temperature oil bath whose temperature was maintained at 120±2° C. 10 mmol styrene along with 20 ml N,N-dimethylformamide (DMF) and 200 mg catalyst were added to the flask. The reaction was started by bubbling oxygen into the reaction mixture at the rate of 3-5 ml $min^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 99.9% styrene conversion with 77.3% styrene oxide selectivity was observed during the reaction.

EXAMPLE 45

The catalytic epoxidation reactions were carried out in liquid phase as a batch reaction at 100° C. using the catalyst prepared by the method described in Example 19(BaCoX 15). A round bottom flask equipped with an efficient water condenser is kept in a constant temperature oil bath whose temperature was maintained at 150±2° C. 10 mmol styrene along with 20 ml N,N-dimethylformamide (DMF) and 200 mg catalyst were added to the flask. The reaction was started by bubbling oxygen into the reaction mixture at the rate of 3-5 ml $min^{-1}$. Tridecane was used as internal standard. The reaction mixture was magnetically stirred. After 4 hours of reaction, the catalyst was separated by centrifuging the reaction mixture and the liquid organic products were analysed with a gas chromatograph. The styrene conversion was calculated using internal standard method. 99.9% styrene conversion with 53.7% styrene oxide selectivity was observed during the reaction.

EXAMPLE 46

The catalytic epoxidation reactions were carried out in liquid phase as a batch reaction in an autoclave reactor at 100° C. using the catalyst prepared by the method described in Example 19 (BaCoX 15). Reactions were carried out in a 100 ml stainless steel autoclave reactor (Autoclave Engineers, USA) equipped with a controlling unit. 25 mmol styrene along with 50 ml N,N-dimethylformamide (DMF) and 500 mg catalyst were charged in the autoclave. Oxygen at 5000 Torr pressure was introduced in to the reactor. The reactor was then brought to the desired reaction temperature and the epoxidation reaction was then initiated by starting the stirrer. Tridecane was used as internal standard. After 4 hours of reaction, the catalyst was separated by centrifuging the reaction mixture and the liquid organic products were analysed with a gas chromatograph. The styrene conversion was calculated using internal standard method. 98.9% styrene conversion with 84.1% styrene oxide selectivity was observed during the reaction.

EXAMPLE 47

The catalytic epoxidation reactions were carried out in liquid phase as a batch reaction in an autoclave reactor at 100° C. using the catalyst prepared by the method described in Example 19 (BaCoX 15). Reactions were carried out in a 100 ml stainless steel autoclave reactor (Autoclave Engineers, USA) equipped with a controlling unit. 25 mmol styrene along with 50 ml N,N-dimethylformamide (DMF) and 500 mg catalyst were charged in the autoclave. Oxygen at 10000 Torr pressure was introduced in to the reactor. The reactor was then brought to the desired reaction temperature and the epoxidation reaction was then initiated by starting the stirrer. Tridecane was used as internal standard. After 4 hours of reaction, the catalyst was separated by centrifuging the reaction mixture and the liquid organic products were analysed with a gas chromatograph. The styrene conversion was calculated using internal standard method. 99.9% styrene conversion with 84.2% styrene oxide selectivity was observed during the reaction.

EXAMPLE 48

The catalytic epoxidation reactions were carried out in liquid phase as a batch reaction in an autoclave reactor at 100° C. using the catalyst prepared by the method described in Example 19 (BaCoX 15). Reactions were carried out in a 100 ml stainless steel autoclave reactor (Autoclave Engineers, USA) equipped with a controlling unit. 25 mmol styrene along with 50 ml N,N-dimethylformamide (DMF) and 500 mg catalyst were charged in the autoclave. Oxygen at 20000 Torr pressure was introduced in to the reactor. The reactor was then brought to the desired reaction temperature and the epoxidation reaction was then initiated by starting the stirrer. Tridecane was used as internal standard. After 4 hours of reaction, the catalyst was separated by centrifuging the reaction mixture and the liquid organic products were analysed with a gas chromatograph. The styrene conversion was calculated using internal standard method. 99.9% styrene conversion with 84.0% styrene oxide selectivity was observed during the reaction.

TABLE 1

Styrene Conversion, Styrene oxide Selectivity and TOF

| Example No. | % Styrene Conversion | % Styrene oxide Selectivity | TOF |
| --- | --- | --- | --- |
| Example 1 | 2.5 | 56.5 | — |
| Example 2 | 66.0 | 66.9 | 25.3 |
| Example 3 | 77.9 | 67.5 | 15.9 |
| Example 4 | 87.6 | 65.1 | 9.7 |
| Example 5 | 97.2 | 67.7 | 5.6 |
| Example 6 | 97.9 | 68.0 | 4.8 |
| Example 7 | 98.4 | 66.4 | 4.2 |
| Example 8 | 41.8 | 67.8 | 1.8 |
| Example 9 | 64.9 | 66.9 | 2.8 |
| Example 10 | 98.4 | 66.4 | 4.2 |
| Example 11 | 99.9 | 65.3 | 4.2 |
| Example 12 | 99.8 | 66.9 | 4.1 |
| Example 13 | 98.7 | 71.3 | 22.7 |
| Example 14 | 98.6 | 71.8 | 24.0 |
| Example 15 | 99.8 | 76.6 | 26.4 |
| Example 16 | 99.5 | 74.6 | 21.1 |
| Example 17 | 99.8 | 82.9 | 24.9 |
| Example 18 | 99.9 | 85.1 | 27.4 |
| Example 19 | 99.9 | 82.6 | 32.5 |
| Example 20 | 99.4 | 80.4 | 27.8 |
| Example 21 | 99.8 | 83.1 | 26.9 |
| Example 22 | 99.6 | 81.0 | 26.5 |

TABLE 1-continued

Styrene Conversion, Styrene oxide Selectivity and TOF

| Example No. | % Styrene Conversion | % Styrene oxide Selectivity | TOF |
| --- | --- | --- | --- |
| Example 23 | 99.2 | 66.4 | 4.2 |
| Example 24 | 99.4 | 65.5 | 4.0 |
| Example 25 | 98.7 | 71.3 | 22.7 |
| Example 26 | 99.8 | 76.9 | 26.6 |
| Example 27 | 99.8 | 83.8 | 25.3 |
| Example 28 | 99.9 | 85.9 | 27.7 |
| Example 29 | 99.9 | 83.9 | 33.0 |
| Example 30 | 98.4 | 66.4 | 4.2 |
| Example 31 | 99.3 | 67.2 | 4.3 |
| Example 32 | 99.2 | 66.9 | 4.2 |
| Example 33 | 99.9 | 85.1 | 27.4 |
| Example 34 | 99.9 | 85.3 | 27.5 |
| Example 35 | 99.9 | 82.6 | 32.5 |
| Example 36 | 99.8 | 82.9 | 32.7 |
| Example 37 | 89.0 | 63.1 | 10.1 |
| Example 38 | 92.0 | 61.0 | 9.8 |
| Example 39 | 86.0 | 56.2 | 8.7 |
| Example 40 | 80.1 | 51.9 | 7.9 |
| Example 41 | 93.6 | 73.1 | 18.1 |
| Example 42 | 99.1 | 85.9 | 27.4 |
| Example 33 | 39.9 | 84.9 | 22.7 |
| Example 44 | 99.9 | 77.3 | 30.5 |
| Example 45 | 99.9 | 53.7 | 18.9 |
| Example 46 | 98.9 | 84.1 | 32.9 |
| Example 47 | 99.9 | 84.2 | 33.5 |
| Example 48 | 99.9 | 84.0 | 33.2 |

We claim:

1. A process for the catalytic epoxidation of styrene with molecular oxygen using metal ion exchanged zeolite, which comprises reacting styrene with air or molecular oxygen in an organic solvent, in the presence of a zeolite based catalyst having the general formula $(CoO)_a \cdot (M_{2/n}O)_b \cdot (Al_2O_3)_c \cdot (SiO_2)_d \cdot wH_2O$, wherein the values of a varies from 8 to 48; b varies from 0 to 80 with 2a+b=c, w being the number of moles of water varies from 0 to 200 and M is alkali and/alkaline earth metal ion having valancy n, where n is +1 or +2, at a temperature in the range of 80-150° C., for a period of 3-6 hrs, separating the catalyst from the above said reaction mixture by known methods to obtain the desired product.

2. A process as claimed in claim 1, wherein the organic solvent used is selected from the group consisting of N,N-dimethylformamide (DMF), N,N-dimethylacetamide (DMA) and 1,4-dioxan.

3. A process as claimed in claim 1, wherein the flow rate of air or molecular oxygen used is in the range of 3-5 ml per min.

4. A process as claimed in claim 1, wherein the pressure of air or molecular oxygen used is in the range of 760 to 20000 Torr.

5. A process as claimed in claim 1, wherein the zeolite catalyst used is dried at a temperature of 20-30° C. to retain the adsorbed water molecules inside the zeolite cavities.

6. A process as claimed in claim 1, wherein the alkali and/or alkaline earth metal cationic promoter used in zeolite catalyst is selected from the group consisting of lithium, sodium, potassium, rubidium, cesium, magnesium, calcium, strontium, barium and a combination thereof.

7. A process as claimed in claim 1, wherein the % conversion of styrene obtained is in the range of 70-99.9%.

8. A process as claimed in claim 1, wherein the selectivity of the styrene oxide obtained is in the range of 60-90%.

* * * * *